(12) United States Patent
Bonmann et al.

(10) Patent No.: US 7,799,958 B2
(45) Date of Patent: Sep. 21, 2010

(54) PROCESS FOR THE PRODUCTION OF ISO-PROPANOL BY LIQUID PHASE HYDROGENATION

(75) Inventors: Ralf Bonmann, Hattingen (DE); Werner Pompetzki, Dorsten (DE); Markus Weber, Haltern (DE)

(73) Assignee: Barclays Bank PLC, London (GB)

( * ) Notice: Subject to any disclaimer, the term of this patent is extended or adjusted under 35 U.S.C. 154(b) by 1 day.

(21) Appl. No.: 12/245,598

(22) Filed: Oct. 3, 2008

(65) Prior Publication Data

US 2009/0093656 A1 Apr. 9, 2009

Related U.S. Application Data

(60) Provisional application No. 60/977,555, filed on Oct. 4, 2007.

(51) Int. Cl.
*C07C 29/143* (2006.01)
*C07C 29/145* (2006.01)
*C07C 37/08* (2006.01)

(52) U.S. Cl. .................. 568/881; 568/880; 568/798

(58) Field of Classification Search .................. 568/798
See application file for complete search history.

(56) References Cited

U.S. PATENT DOCUMENTS

| | | | | |
|---|---|---|---|---|
| 4,960,960 | A | | 10/1990 | Harrison et al. |
| 5,160,497 | A | | 11/1992 | Juguin et al. |
| 5,866,725 | A | * | 2/1999 | Unruh et al. ............. 568/881 |
| 5,868,906 | A | * | 2/1999 | Adams et al. ............. 203/18 |
| 5,897,750 | A | | 4/1999 | Berg |
| 6,307,112 | B1 | * | 10/2001 | Weber et al. ............. 568/798 |
| 6,657,087 | B2 | * | 12/2003 | Weber et al. ............. 568/385 |
| 6,841,704 | B2 | * | 1/2005 | Sakuth et al. ............. 568/798 |
| 6,930,213 | B1 | * | 8/2005 | Pompetzki et al. ......... 568/883 |
| 2005/0034970 | A1 | * | 2/2005 | Schwarz et al. ............. 203/22 |

FOREIGN PATENT DOCUMENTS

| | | | |
|---|---|---|---|
| EP | 0379803 | B1 | 2/1994 |
| EP | 0371738 | B1 | 3/1994 |
| EP | 0361755 | B1 | 6/1994 |
| EP | 0379323 | B1 | 3/1995 |
| EP | 0498573 | B1 | 8/1996 |
| EP | 1070698 | A2 | 1/2001 |
| WO | WO 01/62692 | A1 | 8/2001 |
| WO | WO0162692 | * | 8/2001 .......... 568/798 |
| WO | WO 03/011801 | A2 | 2/2003 |

OTHER PUBLICATIONS

Schultz et al., 98 Chem. Eng. Prog., 64-71(2002).*

* cited by examiner

*Primary Examiner*—Brian J Davis
(74) *Attorney, Agent, or Firm*—Knobbe Martens Olson & Bear LLP

(57) ABSTRACT

The present invention relates to a process for the production of iso-propanol by liquid phase hydrogenation of acetone to iso-propanol in at least two hydrogenation reaction stages, each reaction stage comprising a hydrogenation reaction zone, wherein the hydrogenation reaction product leaving the reaction zone of the first reaction stage contains unreacted acetone and a product stream comprising acetone and iso-propanol is transferred to the reaction zone of a subsequent reaction stage said product stream having at the inlet to the reaction zone of said subsequent reaction stage a temperature of 60 to 100° C., wherein the temperature of the product stream leaving the reaction zone of said subsequent reaction stage at the outlet from said reaction zone is at most 40° C. higher than the temperature of the product stream entering said reaction zone at the inlet to said reaction zone and the temperature in said subsequent reaction zone does not exceed 125° C., to a process of purifying an iso-propanol raw product containing less than 1,000 wppm acetone comprising subjecting the iso-propanol raw product to a distillation in a dividing wall distillation column to obtain purified iso-propanol and to an integrated process for the production of phenol employing the above hydrogenation process.

34 Claims, 1 Drawing Sheet

US 7,799,958 B2

PROCESS FOR THE PRODUCTION OF ISO-PROPANOL BY LIQUID PHASE HYDROGENATION

CROSS-REFERENCE TO RELATED APPLICATIONS

This application is a non-provisional application of Provisional Application No. 60/977,555, filed Oct. 4, 2007, the entire disclosure of which is expressly incorporated herein by reference in its entirety.

FIELD OF THE INVENTION

The present invention relates to a process for the production of iso-propanol by liquid phase hydrogenation of acetone to iso-propanol in at least two hydrogenation reaction stages. Furthermore, the present invention relates to the purification of thus obtained iso-propanol by means of a separation train including a dividing wall distillation column.

Additionally, the present invention relates to an integrated process for the production of phenol according to the well-known Hock process whereby the acetone obtained as a by-product is hydrogenated according to the process of the present invention and either directly recycled into the step of making cumene or is first dehydrated to obtain propene that is then reacted with benzene in order to produce cumene.

DESCRIPTION OF THE RELATED ART

Presently the vast majority of commercial phenol is produced according to the Hock process. In general In the Hock process benzene is first alkylated to produce cumene. The cumene is subsequently oxidized to cumene hydroperoxide and thereafter catalytically cleaved to phenol and acetone whereby both products are isolated after appropriate work-up and purifications steps.

Consequently, the Hock process for making phenol inevitably produces acetone as a couple product.

Commercial processes that result in couple product formation have inherently the disadvantage that, if the demand for one product on the world market develops differently from the demand for the other product, a surplus of couple product is produced that is difficult to sell with a negative influence on prices and thus on the economics of the whole process.

Presently the demand for phenol is higher than the demand for acetone. Consequently there have been numerous attempts to avoid the couple product formation of acetone.

EP 0361755 discloses an integrated process for making phenol comprising the steps of alkylation of benzene with propene to obtain cumene, oxidation of cumene to cumene hydroperoxide, acid cleavage of cumene hydroperoxide to produce phenol and acetone, hydrogenation of acetone and dehydration of isopropanol in order to obtain propene that is subsequently fed to the first step of alkylation of benzene with propene. The hydrogenation step of acetone is conducted in a single tube reactor using Raney nickel in presence of considerable amounts of water. Furthermore, still 0.2 wt.-% of acetone remains in the reaction product. The use of Raney nickel in combination with high amounts of water has the disadvantage that the work-up of the resulting iso-propanol is hampered due to the formation of water iso-propanol azeotropes.

A similar process is described in EP 0371738 wherein the iso-propanol obtained from the hydrogenation step is directly used as alkylation agent in the alkylation of benzene to obtain cumene. The hydrogenation of acetone described in that reference is also similar using Raney nickel in presence of water whereby acetone conversion is only 99% and the Iso-propanol yield is 98.7%.

EP 0379323 describes hydrogenation of acetone to iso-propanol using Raney nickel as hydrogenation catalyst in presence of water in a trickle bed reactor. In the examples acetone conversions between 95 and 99.9% are given. Thus, this process has still the disadvantage of a hydrogenation reaction in presence of water. Furthermore, the experimental data imply that acetone conversion is highly susceptible to the flow condition selected for the trickle bed reactor with the result that even small instabilities during the hydrogenation will result in an acetone conversion that is difficult to control.

EP 0498573, EP 0379803, EP 0498573 and EP 0379803 disclose different processes for the dehydration of iso-propanol to propene.

U.S. Pat. No. 5,160,497 similarly discloses an integrated process for the production of phenol wherein benzene is reacted with propene and iso-propanol to obtain a mixture of non-converted benzene, cumene and poly-isopropyl benzenes. The poly-isopropyl benzene fraction is then contacted with a dealuminized y-zeolite to obtain cumene. Cumene is then converted into a mixture of acetone and phenol and acetone is hydrogenated to iso-propanol and recycled to the alkylation step. Example 4 of that reference describes the hydrogenation of acetone to isopropanol whereby the molar ratio of iso-propanol to acetone of the feed stream is 6.6 and the inlet temperature into the reactor is 80° C. and the outlet temperature 10 of the reactor is 130° C. The feedstock comprises 85.09% iso-propanol and 12.72% acetone.

WO 01/62692 describes an integrated process for making phenol from benzene comprising alkylation of benzene with iso-propanol or a mixture of iso-propanol and propene to cumene, oxidizing cumene to cumene hydroperoxide, acid cleavage of cumene hydroperoxide to give phenol and acetone and hydrogenating acetone to form iso-propanol by hydrogenation of acetone in at least two process stages. The hydrogenation step is described in more detail in EP 1070698. The example in that reference describes a two stage hydrogenation process wherein in a first stage a loop reactor is used and in the second stage a tube reactor. The process conditions for the loop reactor are 70° C. inlet temperature, 115° C. outlet temperature, circulation ratio of 1 to 8 resulting in a reaction product containing 12.5 wt.-% acetone and 87.5 wt.-% iso-propanol. This reaction mixture is fed to the second stage having an inlet temperature of 70° C. and an outlet temperature of 126° C. The reaction mixture leaving the second reactor has still 0.54 wt.-% acetone.

U.S. Pat. No. 4,960,960 deals with a two stage liquid phase hydrogenation process whereby as one of several possibilities the hydrogenation of acetone to form isopropanol is disclosed. Reaction conditions are inter alia given for the hydrogenation of an aldehyde whereby the entry temperature to the first hydrogenation zone lies in the range of 90° C.-220° C. and the pressure between 3 bar to 50 bar. No such information is given for the second stage.

WO 03/011801 discloses a one stage process of hydrogenation of acetone containing small amounts of benzene to iso-propanol. As is evident from the process description, especially also FIG. 1 of that reference, complicated workup proceedings involving altogether four distillation columns are necessary to obtain iso-propanol having the desired purity.

U.S. Pat. No. 5,897,750 addresses the problem of removing acetone from a mixture containing acetone, iso-propanol and water by extractive distillation whereby as extractive agents 1-nitropropane, 3-carene, dimethylsulfoxide and 3-pentanone are preferred. From this reference it is evident that iso-propanol containing acetone and water is difficult to purify in order to obtain iso-propanol of the desired grade.

Furthermore, from the prior art discussed above it is evident that, although hydrogenation of acetone to form iso-propanol is in principle known, there is still a desire to optimize the hydrogenation conditions in order to achieve a reaction product that contains only very limited amounts of acetone. This is especially important when this hydrogenation step is part of an integrated phenol process since acetone is obtained in the phenol process in very high amounts and even small losses of acetone in the hydrogenation step would result in a considerable total loss of material which is economically disadvantageous.

Furthermore, it is an object of the present invention to simplify the purification steps of an iso-propanol obtained from the hydrogenation of acetone.

It is another object of the present invention to provide a process for preparation of iso-propanol starting from acetone that leads into a highly pure iso-propanol that does not necessarily have to be integrated into a phenol process and thus allows direct marketing of the obtained iso-propanol which increases the commercial flexibility of phenol producers.

SUMMARY OF THE INVENTION

The above defined objects have been attained by a process for the production of iso-propanol by liquid phase hydrogenation of acetone to iso-propanol in at least two hydrogenation reaction stages, each reaction stage comprising a hydrogenation reaction zone, wherein the hydrogenation reaction product leaving the reaction zone of the first reaction stage contains unreacted acetone and a product stream comprising acetone and iso-propanol is transferred to the reaction zone of a subsequent reaction stage said product stream having at the inlet to the reaction zone of said subsequent reaction stage a temperature of 60 to 100° C., whereby the temperature of the product stream leaving the reaction zone of said subsequent reaction stage at the outlet from said reaction zone is at most 40° C. higher than the temperature of the product stream entering said reaction zone at the inlet to said reaction zone and the temperature in said subsequent reaction zone does not exceed 125° C.

It has been surprisingly discovered that in a two stage liquid phase hydrogenation process the total conversion of acetone can be further increased if the temperature increase in a reaction zone subsequent to the first reaction zone between outlet temperature of that zone and the inlet temperature into that zone is limited. From the examples in EP 1070698 it is evident that with a temperature increase for the second reaction stage between outlet temperature and inlet temperature of more than 50° C. still unwanted high amounts of acetone are present In the hydrogenation product.

In contrast thereto, when limiting the temperature increase between outlet temperature and inlet temperature to 40° C. at most, the amount of unreacted acetone in the hydrogenation product can be further reduced.

Thus, the hydrogenation process of the present invention has several advantages. First of all, loss of acetone is reduced with the result that the hydrogenation process according to the present invention can be advantageously integrated into a process for the production of phenol, thereby further increasing the economic efficiency of these processes.

Consequently, the above objects are also attained by a process for the production of phenol comprising:

a) alkylating benzene in the presence of iso-propanol to obtain cumene;

b) oxidizing cumene with an oxygen containing medium to obtain cumene hydroperoxide;

c) cleaving cumene hydroperoxide in presence of an acidic catalyst to obtain phenol and acetone;

d) separating the product obtained in step c) into a phenol containing stream and into an acetone containing stream;

e) optionally purifying the acetone containing stream obtained in step d) to obtain purified acetone;

f) optionally purifying the phenol containing stream obtained In step d) to obtain purified phenol;

g) hydrogenating the acetone containing stream of step d) and/or the purified acetone of step e) to obtain iso-propanol;

h) recycling the iso-propanol of step g) to step a);

characterized in that step g) is conducted by employing the hydrogenation process according to the present invention, and a process for the production of phenol comprising:

a) alkylating benzene with propene to obtain cumene;

b) oxidizing cumene with an oxygen containing medium to obtain cumene hydroperoxide;

c) cleaving cumene hydroperoxide in presence of an acidic catalyst to obtain phenol and acetone;

d) separating the product obtained in step c) into a phenol containing stream and into an acetone containing stream;

e) optionally purifying the acetone containing stream obtained in step d) to obtain purified acetone;

f) optionally purifying the phenol containing stream obtained in step d) to obtain purified phenol;

g) hydrogenating the acetone containing stream of step d) and/or the purified acetone of step e) to obtain iso-propanol;

h) dehydrating the iso-propanol of step g) to obtain propene;

i) optionally purifying the propene of step h);

j) recycling the propene of step h) and/or the purified propene of step i) to step a), characterized in that step g) is conducted by employing the hydrogenation process according to the present invention.

Another advantage of obtaining iso-propanol with a low amount, for example less than 1,000 wppm of acetone, is that the work-up procedure, as for example known from WO 03/011801, can be considerably simplified.

Consequently, one of the above objects is also attained by a process of purifying an iso-propanol raw product containing less than 1000 wppm acetone comprising subjecting the iso-propanol raw product to a distillation in a dividing wall distillation column to obtain purified iso-propanol.

This purification process step can be easily incorporated into the overall process of producing iso-propanol by liquid phase hydrogenation of acetone. Thereby an iso-propanol of high purity is obtained that can be either directly marketed or recycled directly into the process for making phenol or via a further dehydration step to produce propene.

DETAILED DESCRIPTION OF THE PREFERRED EMBODIMENT

Figure 1:
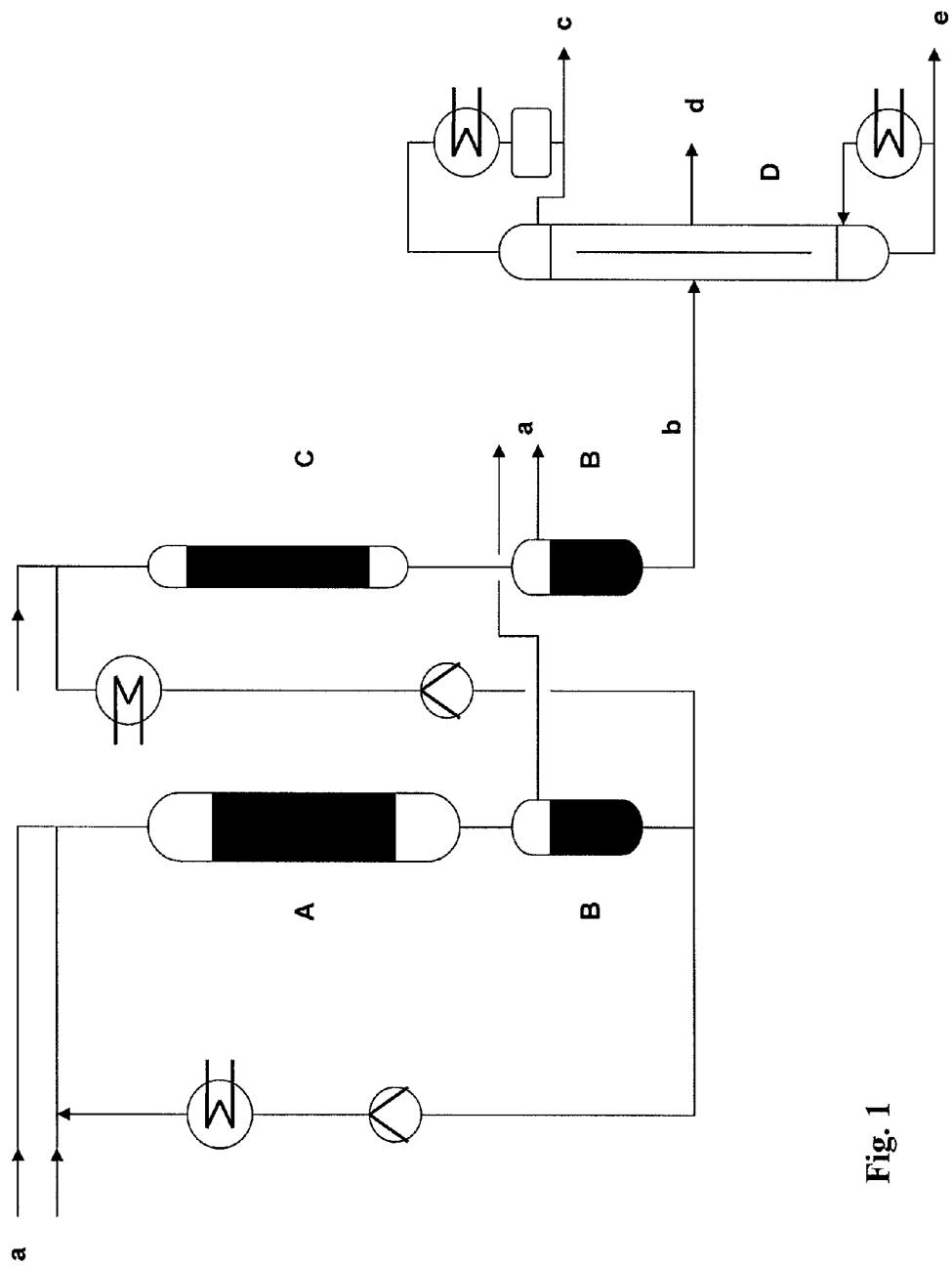
FIG. 1. Flow scheme of circulation and tube reactors. (A) Upstream circulation reactor, (B) intermediate cooling in apparatus component and (C) tube reactor. The hydrogen feed and discharge lines are denoted a) and the product line is denoted by (b). Reaction product obtained from the second reactor (C) is directed to a dividing wall distillation column (D) via line (b) wherein impurities are removed as head product via line (c) and bottom product via line (e) and the highly purified isopropanol is obtained at the side take-off of column (D) via line (d).

According to the present invention, a product stream from the hydrogenation of acetone, comprising acetone and iso-propanol obtained from one or a plurality of reaction zones connected in series, is supplied to a subsequent reaction zone. Thereby, the temperature of the product stream at the inlet to said subsequent reaction zone ranges from 60 to 100° C.

The hydrogenation reaction of acetone to iso-propanol is in general exothermic, thus the temperature at the outlet of said subsequent reaction zone will be higher than the temperature at the inlet to this reaction zone, if not cooled.

According to the present invention, this temperature increase within that subsequent reaction zone is limited to 40° C. at most.

According to a preferred embodiment of the present invention, the temperature of the product stream at the Inlet to said subsequent reaction zone ranges from 60 to 90° C. and more preferred from 60 to 80° C.

Furthermore, the increase of the temperature of the product stream at the outlet of said subsequent reaction zone compared to the temperature at the inlet of said reaction zone is preferably 30° C. at most, more preferred 20° C. at most, and most preferred 10° C. at most.

Although it is in principle possible to operate the above-discussed subsequent process stage isothermically, it is preferred that the temperature increase between outlet temperature and inlet temperature of said reaction zone is at least 5° C. By allowing some temperature increase within the limits of the present invention heat removal can be less stringent and the reaction volume can be lower compared to a strictly isothermal regime. Thus an optimal balance between the objects of the present invention as discussed above and low investment and operating costs is achieved.

The maximum temperature in said subsequent reaction zone should not exceed 125° C., preferably 120° C.

According to a preferred embodiment of the process according to the present invention, the process is conducted in two stages. Thereby preferably the first reaction stage comprises a loop reactor and the second reaction stage comprises a tube reactor. The advantages using a loop reactor is that the circulation ratio can be easily adjusted In order to achieve an appropriate dilution of the acetone stream entering the reactor.

The same effect can be also be achieved by using a diluent, preferably the reaction product iso-propanol. Consequently, it is also possible to admix acetone with iso-propanol recycled from the process prior to entry into a conventional tube reactor.

Alternatively, it is also possible to substitute the loop reactor by a series of connected tube reactors with only limited conversion of acetone in each reactor stage with the result that acetone functions as a diluent. A series of connected loop reactors may be also employed.

During the hydrogenation of acetone to iso-propanol a number of unwanted side products can be obtained due to possible condensation of the educt acetone or the product Iso-propanol. Furthermore, some of these by-products react further by elimination of water. All these side reactions result in an undesired loss of material.

For example, after the alkali-catalyzed aldol condensation of acetone to diacetone alcohol, elimination of water leads to 4-methyl-3-penten-2-one (mesityl oxide). The hydrogenation of the intermediate mesityl oxide leads via 4-methyl-2-pentanone (methyl isobutyl ketone) to 4-methyl-2-pentanol. However, diacetone alcohol can also be hydrogenated directly to hexylene glycol. The desired product iso-propanol can also react further with elimination of water to form the undesired diisopropyl ether.

Some of the above-mentioned secondary reactions proceed with the elimination of water. In order to suppress these secondary reactions, i.e. in order to increase selectivity, the addition of a small amount of water is therefore conceivable.

As discussed in the prior art sections, many prior art processes of hydrogenation of acetone to iso-propanol therefore use Raney nickel in presence of water, in order to achieve a high selectivity to iso-propanol.

This additional water, which is undesirable in some specific uses of iso-propanol, remains in the product mixture and may have to be removed, which is, especially in combination with acetone, difficult to achieve due to the formation of azeotropes.

In contrast thereto, the present invention makes it possible to hydrogenate acetone containing a very small amount of more water. In the process of the invention acetone having a water content of less than or equal to 1 wt.-%, preferably less than or equal to 0.5 wt.-%, most preferred less than 0.2 wt.-% can be hydrogenated to form iso-propanol with a high selectivity.

Suitable catalysts for the process of the present invention are selected from catalysts comprising nickel as active component on a neutral support. Preferably, the neutral support is α-aluminum oxide.

In the following descriptions for the reaction conditions in the several stages of the hydrogenation process, it is distinguished between reaction stages wherein the reaction conditions can be widely varied and the reaction stages requiring the specific temperature control according to the present invention. The first type of reaction stages will be defined in the following for ease of description as "other reaction stages or other reaction zones," the latter type of process stages requiring the specific temperature control according to the present invention is defined as "subsequent reaction stage or subsequent reaction zone".

The total number of subsequent reaction zones and other reaction zones is not critical to the present invention as long as there is a first other reaction stage and at least one subsequent reaction stage in the succession of reaction zones of the multi-stage hydrogenation process.

It is preferred that in a sequence of reaction stages the subsequent reaction stage is the last reaction stage since in this stage any remaining acetone is hydrogenated in order to achieve a quantitative or close to quantitative conversion of acetone. However, it is conceivable according to the present invention to have more than one subsequent reaction stage at the end of the successive reaction stages. As mentioned above, according to a preferred embodiment, the hydrogenation is conducted in two stages with a first other reaction stage and one subsequent reaction stage.

The reaction conditions for the other reaction stages can be varied within wide limits, i.e., the liquid phase hydrogenation can be conducted at a temperature of 60 to 140° C., preferably 70 to 130° C., and a pressure of 10 to 50 bar, preferably 20 to 35 bar. The temperature and pressure conditions can differ in the various other reaction stages.

Depending on the temperature of the product stream, leaving the other reaction stage, the product stream has to be cooled to a temperature of 60 to 100° C. at the inlet point of the subsequent reaction stage. Such cooling, if necessary, can be conducted by any means known by a person skilled in the art, such as by means of a heat exchanger.

The hydrogenation reaction of acetone to iso-propanol is in general exothermic so that in the subsequent reaction stage measures have to be taken in order to limit the temperature increase within the subsequent reaction stage so that the temperature of the reaction stream at the outlet of the subsequent reaction zone is not more than 40° C. higher than the temperature of the reaction stream at the inlet to said reaction zone.

This limitation of the temperature increase in the subsequent reaction zone can be achieved by any suitable means, for example by cooling means. The pressure in the subsequent reaction stage preferably ranges from 10 to 50 bar, particularly preferred from 20 to 35 bar.

In the hydrogenation process according to the present invention in general an excess of hydrogen is employed. The molar ratio of hydrogen to acetone, preferably ranges from 5:1 to 1:1, more preferred from 3:1 to 1:1 and most preferred from 1.5:1 to 1:1.

In one embodiment of the present invention, the liquid stream comprising acetone is directed co-currently with the hydrogen stream through the hydrogen zone of any of the reaction stages. Thereby it is preferred that co-current flow of both streams is maintained in all reaction stages. But it is of course also possible to select different flow regimes for different reaction stages.

The process according to the present invention is preferably conducted continuously, but a batchwise process regime is also possible.

The product obtained by the hydrogenation process of the present invention contains preferably less than 1,000 wppm, more preferred less than 500 wppm, and most preferred less than 120 wppm acetone. Furthermore, due to the preferred low water content in the reaction mixture during the hydrogenation process, the reaction product obtained by the present process contains very limited amounts of remaining acetone and water, that can be easily purified by subjecting the iso-propanol raw product obtained from the hydrogenation process of the present invention to a distillation in a dividing wall distillation column to recover purified iso-propanol. Any excess of hydrogen is preferably separated from the reaction product before entering the distillation column and recycled to the process of the present invention. Thereby, the purified iso-propanol is obtained as side product from the dividing wall distillation column. The advantage of using a dividing wall distillation column is that the raw iso-propanol can be purified in a single work-up stage to a highly purified iso-propanol. Thus, the present invention, contrary to the prior art references discussed in the prior art section, does neither require extractive distillation needing recovery of the extraction medium which results in increased energy costs nor are multiple distillation steps necessary resulting in high investment and operating costs.

Thus, employing a dividing wall column in the distillation of iso-propanol raw products leads to an improved iso-propanol purity in only one distillation stage. The use of a dividing wall column is particularly advantageous in combination with the hydrogenation process of the present invention since the iso-propanol obtained therefrom contains only limited amounts of unreacted acetone, water and unwanted side products so that in the dividing wall column only very low amounts of head and bottom products containing the impurities have to be removed. Thus, the purified iso-propanol obtained as a side take-off from the dividing wall column contains very little amounts of water, preferably less than 2,000 wppm, more preferred less than 1,000 wppm water, most preferred less than 100 wppm water. These low amounts of water make it possible to further dry the resulting product effectively using a molecular sieve 3 Å or 4 Å. The drying step proceeds at a temperature of 25-50° C. The molecular sieve can be easily regenerated by using a regeneration gas having a low relative humidity.

The thus obtained highly purified and dry iso-propanol can be independently marketed or recycled to directly or via intermediate dehydration to propene alone or in mixture with propene to the alkylation step of benzene for making cumene in an integrated phenol process.

The phenol process is conducted in accordance with the well-known Hock process. Thus, any further detailed description of the integrated phenol process is not deemed to be necessary since it belongs to the general knowledge of a person skilled in the art in the field of the production of phenol.

The present invention will now be discussed in more detail with reference to the schematic flow diagram in FIG. 1 showing a preferred embodiment according to the present invention comprising a circulation reactor for the other process stage and a tube reactor for the subsequent process stage.

The flow scheme shows upstream circulation reactor (A) with the ability to recycle a product. The conversion which occurs here is a major part of the required hydrogenation conversion. Reactor (A) generally operates at a high concentration level and can be operated using a small circulation ratio. The product from the circulation reactor depending on the temperature of the product stream at the outlet of the circulation reactor can then be subjected to intermediate cooling in apparatus component (B). The hydrogenation in the final conversion step is conducted in a shaft oven (C) which operates as a tube reactor without product circulation. The hydrogen feed and discharge lines are denoted a) and the product line is denoted by (b). Reactor (A) is designed as an adiabatic reactor whereas reactor (C) can contain cooling means, like heat exchange means, in order to limit the temperature increase in that reactor in accordance with the present invention.

The starting temperature of the first process stage ranges from 50 to 100° C., and the total pressure ranges from 10 to 50 bar. The circulation ratio may range from 6 to 10. The concentration of acetone in the circulating stream drops by 8 to 20 wt.-% while the concentration of iso-propanol increases by the corresponding amount. Furthermore, due to the adiabatic character of the recirculation reactor, the temperature increases to a range of 100 to 130° C. The product stream leaving the circulating reactor is cooled in the cooling means (B) to a temperature in the range of 60 to 100° C. prior to entering the tube reactor (C). Thus, the temperature of the product stream at the inlet of the second reactor is between 60 and 100° C. In the second reactor the temperature increase can be limited by cooling means (not shown). The pressure is within the range of 10 to 50 bar, preferably 20 to 35 bar. The hydrogenation catalyst used in both stages is preferably nickel on $\alpha\text{-}Al_2O_3$.

The reaction product obtained from the second reactor (C) Is directed to a dividing wall distillation column (D) via line (b) wherein impurities are removed as head product via line (c) and bottom product via line (e) and the highly purified isopropanol is obtained at the side take-off of column (D) via line (d).

The following examples are conducted in accordance with the teaching of the example in EP 1070698.

Example 1

The reaction conditions of the comparative example 1, corresponding to Example 1 of EP 1070698, as well as of Example 1 according to the present invention as well as the results are summarized in Table 1.

TABLE 1

|  | Comparative Example 1 | | Example 1 | |
|---|---|---|---|---|
| Circulation Reactor of the 1st reaction stage: | | | | |
| Inlet temperature | 70° C. | | 70° C. | |
| Outlet temperature | 115° C. | | 115° C. | |
| Circulation ratio | 1:8 | | 1:8 | |
|  | Inlet | Outlet | Inlet | Outlet |
| Acetone | 22.2 wt.-% | 12.5 wt.-% | 22.2 wt.-% | 12.5 wt.-% |
| Iso-propanol | 77.8 wt.-% | 87.5 wt.-% | 77.8 wt.-% | 87.5 wt.-% |
| Tube reactor of the 2nd reaction stage: | | | | |
| Inlet temperature | 70° C. | | 70° C. | |
| Outlet temperature | 126° C. | | 79° C. | |
|  | Inlet | Outlet | Inlet | Outlet |
| Acetone | 12.5 wt.-% | 0.54 wt.-% | 12.5 wt.-% | 106 ppm |
| Iso-propanol | 87.5 wt.-% | 99.45 wt.-% | 87.5 wt.-% | 99.99 wt.-% |

As can be seen from the comparison of both examples, the limitation of the temperature increase in the second reaction stage leads to an increased acetone conversion.

It is understood that the examples and embodiments described herein are for illustrative purposes only and that various modifications or changes in light thereof will be suggested to persons skilled in the art and are to be included within the spirit and purview of this application and scope of any appended claims. All figures, tables, and appendices, as well as publications, patents, and patent applications, cited herein are hereby incorporated by reference in their entirety for all purposes.

What is claimed is:

1. A process for the production of iso-propanol comprising:
hydrogenating acetone to iso-propanol in liquid phase in a first reaction stage comprising a first hydrogenation reaction zone, thereby obtaining a product stream leaving the reaction zone of the first reaction stage containing unreacted acetone and iso-propanol;
transferring the product stream comprising acetone and iso-propanol to a subsequent reaction zone of a subsequent reaction stage, said product stream having at the inlet to the reaction zone of said subsequent reaction stage a temperature of 60 to 100° C.; and hydrogenating acetone in the product stream to iso-propanol in liquid phase in said subsequent reaction stage,
wherein the temperature of the product stream leaving the subsequent reaction zone at an outlet from said subsequent reaction zone is 40° C. or less higher than the temperature of the product stream entering said subsequent reaction zone at the inlet to said subsequent reaction zone and the temperature in said subsequent reaction zone does not exceed 125° C.

2. The process as defined in claim 1, wherein the temperature of the product stream entering the reaction zone of said subsequent reaction stage at the inlet to said reaction zone ranges from 60 to 90° C. and the temperature of the reaction product leaving said reaction zone at the outlet of said reaction zone is at most 30° C. higher than the temperature of the product stream entering said reaction zone at the inlet to said reaction zone.

3. The process as defined in claim 1, wherein the process is conducted in two stages.

4. The process as defined in claim 3, wherein the first reaction stage comprises a loop reactor and the second reaction stage comprises a tube reactor.

5. The process as defined in claim 1, wherein the liquid stream comprising acetone is directed co-currently with the hydrogen stream through the hydrogenation zone of any of the reaction stages.

6. The process as defined in claim 1, wherein the hydrogenation is conducted at a molar ratio of hydrogen to acetone ranging from 5:1 to 1:1.

7. The process as defined in claim 1, wherein the acetone to be hydrogenated comprises less than or equal to 1 wt.-% water.

8. The process as defined in claim 1, wherein the pressure in any of the reaction stages ranges from 10 to 50 bar.

9. The process as defined in claim 1, wherein the temperature in the hydrogenation zone of the first reaction stage ranges from 60 to 130° C.

10. The process as defined in claim 1, wherein the hydrogenation is conducted in presence of a hydrogenation catalyst.

11. The process as defined in claim 10, wherein the hydrogenation catalyst comprises nickel on a neutral support.

12. The process as defined in claim 11, wherein the neutral support is $\alpha$-$Al_2O_3$.

13. The process as defined in claim 1, wherein the obtained product contains less than 1000 wppm acetone.

14. The process as defined in claim 1, further comprising subjecting the iso-propanol raw product obtained from the last reaction stage to a distillation in a dividing wall distillation column to recover purified iso-propanol.

15. The process as defined in claim 14, wherein any excess of hydrogen is separated from the reaction product obtained from the last reaction stage prior to subjecting the iso-propanol raw product to distillation.

16. The process as defined in claim 15, wherein the separated hydrogen is recycled into the hydrogenation process.

17. The process as defined in claim 14, wherein the raw product is separated into a head product, a bottom product and a side product, purified iso-propanol being obtained as side product.

18. The process as defined in claim 14, wherein the purified iso-propanol contains less than 2,000 wppm water.

19. The process as defined in 18, further comprising drying the purified iso-propanol by contacting with a molecular sieve.

20. A process for the production of phenol comprising:
a) alkylating benzene in the presence of iso-propanol to obtain cumene;
b) oxidizing cumene with an oxygen containing medium to obtain cumene hydroperoxide;
c) cleaving cumene hydroperoxide in presence of an acidic catalyst to obtain phenol and acetone;
d) separating the product obtained in step c) into a phenol containing stream and into an acetone containing stream;
e) optionally purifying the acetone containing stream obtained in step d) to obtain purified acetone;

f) optionally purifying the phenol containing stream obtained in step d) to obtain purified phenol;

g) hydrogenating the acetone containing stream of step d) and/or the purified acetone of step e) to obtain iso-propanol in liquid phase in a first reaction stage comprising a first hydrogenation reaction zone, thereby obtaining a product stream leaving the reaction zone of the first reaction stage containing unreacted acetone and iso-propanol;

h) transferring the product stream comprising acetone and iso-propanol to a subsequent reaction zone of a subsequent reaction stage, said product stream having at the inlet to the reaction zone of said subsequent reaction stage a temperature of 60 to 100° C.; and i) hydrogenating acetone in the product stream to iso-propanol in liquid phase in said subsequent reaction stage; and j) recycling the iso-propanol of step g) to step a, wherein the temperature of the product stream leaving the subsequent reaction zone at an outlet from said subsequent reaction zone is 40° C. or less higher than the temperature of the product stream entering said subsequent reaction zone at the inlet to said subsequent reaction zone and the temperature in said subsequent reaction zone does not exceed 125° C.

21. A process for the production of phenol comprising:

a) alkylating benzene with propene to obtain cumene;

b) oxidizing cumene with an oxygen containing medium to obtain cumene hydroperoxide;

c) cleaving cumene hydroperoxide in presence of an acidic catalyst to obtain phenol and acetone;

d) separating the product obtained in step c) into a phenol containing stream and into an acetone containing stream;

e) optionally purifying the acetone containing stream obtained in step d) to obtain purified acetone;

f) optionally purifying the phenol containing stream obtained in step d) to obtain purified phenol;

g) hydrogenating the acetone containing stream of step d) and/or the purified acetone of step e) to obtain iso-propanol in liquid phase in a first reaction stage comprising a first hydrogenation reaction zone, thereby obtaining a product stream leaving the reaction zone of the first reaction stage containing unreacted acetone and iso-propanol;

h) transferring the product stream comprising acetone and iso-propanol to a subsequent reaction zone of a subsequent reaction stage, said product stream having at the inlet to the reaction zone of said subsequent reaction stage a temperature of 60 to 100° C.; and i) hydrogenating acetone in the product stream to iso-propanol in liquid phase in said subsequent reaction stage;

j) dehydrating the iso-propanol of step g) to obtain propene;

k) optionally purifying the propene of step j), and l) recycling the propene of step j) and/or the purified propene of step k) to step a), wherein the temperature of the product stream leaving the subsequent reaction zone at an outlet from said subsequent reaction zone is 40° C. or less higher than the temperature of the product stream entering said subsequent reaction zone at the inlet to said subsequent reaction zone and the temperature in said subsequent reaction zone does not exceed 125° C.

22. The process of claim 2, wherein the temperature of the product stream entering the reaction zone of said subsequent reaction state at the inlet to said reaction zone ranges from 60 to 80° C.

23. The process of claim 2, wherein the temperature of the reaction product leaving said reaction zone at the outlet of said reaction zone is at most 20° C.

24. The process of claim 2, wherein the temperature of the reaction product leaving said reaction zone at the outlet of said reaction zone is at most 10° C.

25. The process as defined in claim 1, wherein the hydrogenation is conducted at a molar ratio of hydrogen to acetone ranging from 3:1 to 1:1.

26. The process as defined in claim 1, wherein the hydrogenation is conducted at a molar ratio of hydrogen to acetone ranging from 1.5:1 to 1:1.

27. The process as defined in claim 1, wherein the acetone to be hydrogenated comprises less than or equal to 0.5 wt.-% water.

28. The process as defined in claim 1, wherein the acetone to be hydrogenated comprises less than or equal to 0.2 wt.-% water.

29. The process as defined in claim 1, wherein the pressure in any of the reaction stages ranges from 20 to 35 bar.

30. The process as defined in claim 1, wherein the temperature in the hydrogenation zone of the first reaction stage ranges from 70 to 120° C.

31. The process as defined in claim 1, wherein the obtained product contains less than 500 wppm acetone.

32. The process as defined in claim 1, wherein the obtained product contains less than 120 wppm acetone.

33. The process as defined in claim 14, wherein the purified iso-propanol contains less than 1,000 wppm water.

34. The process as defined in claim 14, wherein the purified iso-propanol contains less than 100 wppm water.

* * * * *